(12) United States Patent
Tiwari et al.

(10) Patent No.: US 9,271,939 B2
(45) Date of Patent: Mar. 1, 2016

(54) STABILIZED PROLONGED RELEASE PHARMACEUTICAL COMPOSITION COMPRISING ATYPICAL ANTIPSYCHOTIC

(75) Inventors: Sunil Deviprasad Tiwari, Maharashtra (IN); Vijayendrakumar Virendrakumarji Redasani, Maharashtra (IN); Prasad Shrikantrao Joshi, Maharashtra (IN); Vaibhav Narayan Sawarkar, Maharashtra (IN); Ankur Janak Shah, Maharashtra (IN)

(73) Assignee: Inventia Healthcare Private Limited, Maharashtra (IN)

( * ) Notice: Subject to any disclaimer, the term of this patent is extended or adjusted under 35 U.S.C. 154(b) by 5 days.

(21) Appl. No.: 13/634,476

(22) PCT Filed: Mar. 11, 2011

(86) PCT No.: PCT/IB2011/000539
§ 371 (c)(1),
(2), (4) Date: Sep. 12, 2012

(87) PCT Pub. No.: WO2011/114213
PCT Pub. Date: Sep. 22, 2011

(65) Prior Publication Data
US 2013/0012524 A1   Jan. 10, 2013

(30) Foreign Application Priority Data
Mar. 15, 2010  (IN) .......................... 684/MUM/2010

(51) Int. Cl.
*A61K 9/20* (2006.01)
*A61K 9/28* (2006.01)
*A61K 31/519* (2006.01)

(52) U.S. Cl.
CPC ............. *A61K 9/2031* (2013.01); *A61K 9/2018* (2013.01); *A61K 9/2027* (2013.01); *A61K 9/2054* (2013.01); *A61K 9/2853* (2013.01); *A61K 9/2866* (2013.01); *A61K 31/519* (2013.01)

(58) Field of Classification Search
None
See application file for complete search history.

(56) References Cited

U.S. PATENT DOCUMENTS

| | | | |
|---|---|---|---|
| 4,804,663 A | 2/1989 | Kennis et al. | |
| 5,158,952 A | 10/1992 | Janssen et al. | |
| 7,731,947 B2 | 6/2010 | Eliaz et al. | |
| 7,959,938 B2 | 6/2011 | Rohloff et al. | |
| 8,114,430 B2 | 2/2012 | Rohloff et al. | |
| 2003/0157180 A1 | 8/2003 | Francois et al. | |
| 2004/0092534 A1 | 5/2004 | Yam et al. | |
| 2005/0208132 A1 | 9/2005 | Sathyan et al. | |
| 2005/0232995 A1 | 10/2005 | Yam et al. | |
| 2006/0034927 A1 | 2/2006 | Casadevall et al. | |
| 2006/0189635 A1 | 8/2006 | Kramer et al. | |
| 2006/0216242 A1 | 9/2006 | Rohloff et al. | |
| 2006/0246134 A1* | 11/2006 | Venkatesh | 424/469 |
| 2006/0246138 A1 | 11/2006 | Rohloff et al. | |
| 2007/0026067 A1 | 2/2007 | Yam et al. | |
| 2007/0197591 A1 | 8/2007 | Boom et al. | |
| 2007/0197592 A1 | 8/2007 | Boom et al. | |
| 2007/0232624 A1 | 10/2007 | Palumbo et al. | |
| 2008/0214808 A1 | 9/2008 | Spittaels | |
| 2009/0087487 A1* | 4/2009 | Fox | A61K 9/2086 424/468 |
| 2009/0163519 A1 | 6/2009 | Vermeulen et al. | |
| 2009/0202631 A1 | 8/2009 | Yam et al. | |
| 2009/0220611 A1 | 9/2009 | Dargelas et al. | |
| 2009/0227605 A1 | 9/2009 | Kramer et al. | |
| 2010/0022511 A1 | 1/2010 | Liu et al. | |
| 2010/0330150 A1* | 12/2010 | Venkatesh et al. | 424/439 |
| 2011/0027361 A1* | 2/2011 | Murugesan | A61K 9/284 424/465 |
| 2011/0052687 A1* | 3/2011 | Mehta | A61K 9/2846 424/472 |
| 2011/0105536 A1 | 5/2011 | Lewyn-Briscoe et al. | |
| 2011/0177137 A1 | 7/2011 | Chauhan et al. | |
| 2011/0195981 A1 | 8/2011 | Sathyan et al. | |
| 2012/0201886 A1 | 8/2012 | Kshirsagar et al. | |

FOREIGN PATENT DOCUMENTS

| | | |
|---|---|---|
| EP | 1 539 115 B1 | 9/2007 |
| EP | 1 902 715 A2 | 3/2008 |
| EP | 2 485 767 | 4/2011 |
| WO | WO 2004/010981 A1 | 2/2004 |
| WO | WO 2006/085856 A1 | 8/2006 |
| WO | WO 2006/101815 A2 | 9/2006 |
| WO | WO 2006/101815 A3 | 9/2006 |
| WO | WO 2007/050377 A1 | 5/2007 |
| WO | WO 2007/118033 A1 | 10/2007 |

(Continued)

OTHER PUBLICATIONS

Ozeki et al. "Controlled Release of Drug via Methylcellulose-Carboxyvinylpolymer Interpolymer Complex Solid Dispersion". AAPS PharmSciTech 2005; 6 (2) Article 33.*

(Continued)

*Primary Examiner* — Robert A Wax
*Assistant Examiner* — Danah Al-Awadi
(74) *Attorney, Agent, or Firm* — Withers Bergman LLP

(57) ABSTRACT

The present invention provides stabilized prolonged release pharmaceutical compositions comprising atypical antipsychotic drug like paliperidone or pharmaceutically acceptable salts thereof without incorporating surfactant and/or water penetration enhancer. Such compositions are preferably in the form of a matrix wherein one or more release controlling agents are present in and/or on the matrix. Further, such compositions comprise one or more release controlling agent and exhibits desired in vitro release of drug with or without lag period. The invention also provides a process for the preparation of such compositions.

9 Claims, 1 Drawing Sheet

(56) References Cited

FOREIGN PATENT DOCUMENTS

| WO | WO 2008/011596 | * | 1/2008 | |
| WO | WO 2008/011596 A2 | | 1/2008 | |
| WO | WO 2009/025859 A1 | | 2/2009 | |
| WO | WO 2009/026621 A1 | | 3/2009 | |
| WO | WO 2009/036056 A1 | | 3/2009 | |
| WO | WO 2009/036100 A2 | | 3/2009 | |
| WO | WO 2009/055001 A2 | | 4/2009 | |
| WO | WO2009025859 | * | 8/2009 | A61K 9/16 |
| WO | WO 2009/109993 | * | 9/2009 | |
| WO | WO 2009/109993 A1 | | 9/2009 | |
| WO | WO 2009/141309 A1 | | 11/2009 | |
| WO | WO 2010/009900 A1 | | 1/2010 | |
| WO | WO 2010/026254 A1 | | 3/2010 | |
| WO | WO 2010/044097 A2 | | 4/2010 | |
| WO | WO 2011/018246 A2 | | 2/2011 | |
| WO | WO 2011/018246 A3 | | 2/2011 | |
| WO | WO 2011/042453 A1 | | 4/2011 | |
| WO | WO 2011/045774 A2 | | 4/2011 | |
| WO | WO 2011/045774 A3 | | 4/2011 | |
| WO | WO 2011/045774 A4 | | 4/2011 | |
| WO | WO 2011/063732 A1 | | 6/2011 | |
| WO | WO 2012/014052 A2 | | 2/2012 | |

OTHER PUBLICATIONS

Ozeki et al. "Controlled release from solid dispersion composed of poly(ethylene oxide)-carbopol® interpolymer complex with various cross-linking degress of carbopol®". Journal of Controlled Release 63 (2000) 287-295.*

Ozeki et al. "Control of medicine release from solid dispersion through poly(ethylene oxide)-carboxyvinylpolymer interaction". International Journal of Pharamceutics 165 (1998) 239-244.*

* cited by examiner

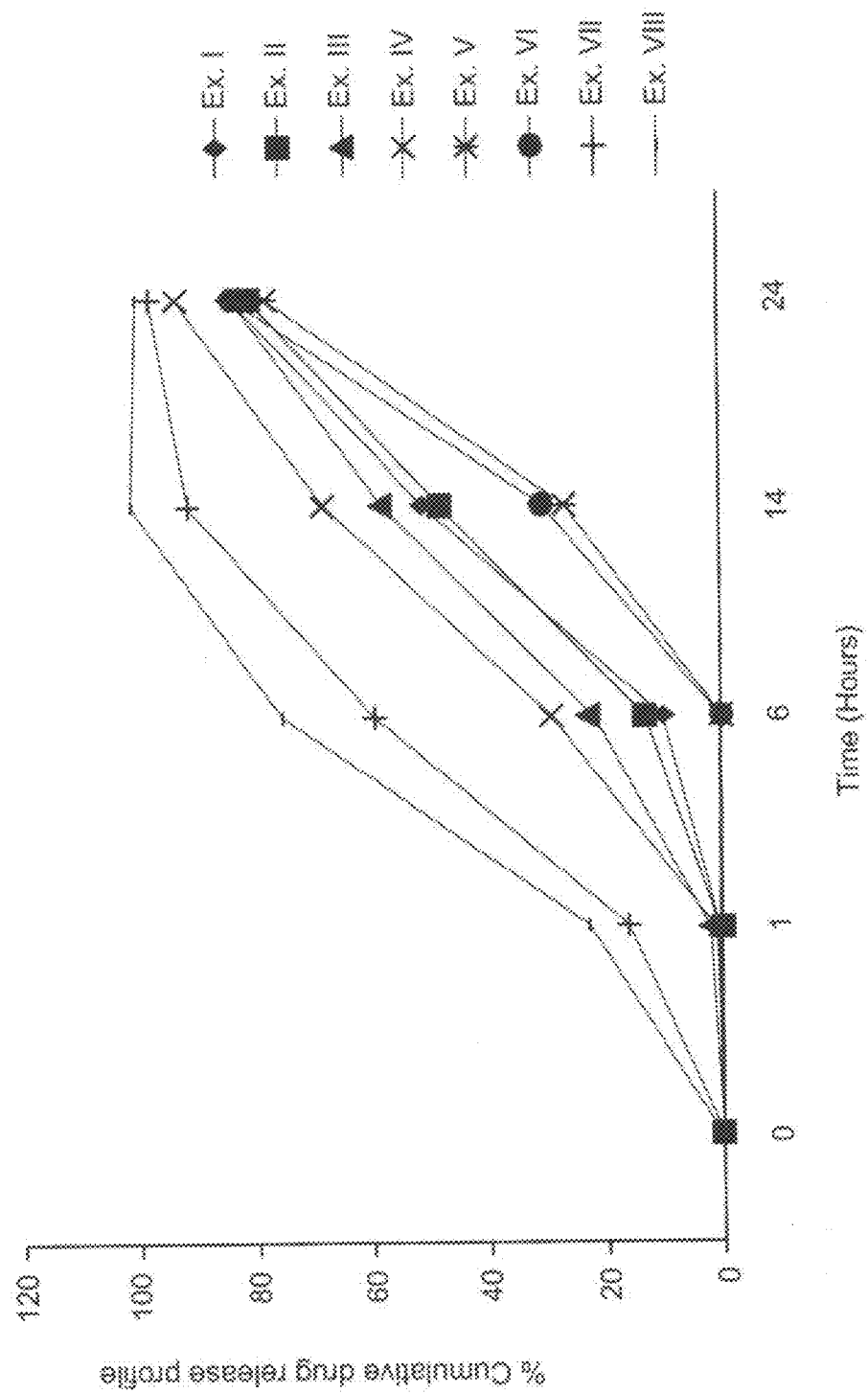

STABILIZED PROLONGED RELEASE PHARMACEUTICAL COMPOSITION COMPRISING ATYPICAL ANTIPSYCHOTIC

FIELD OF THE INVENTION

The present invention relates to stabilized prolonged release pharmaceutical compositions comprising an antipsychotic drug, preferably atypical antipsychotic drug or pharmaceutically acceptable salts thereof, and process for preparation of the same.

BACKGROUND OF THE INVENTION

Paliperidone is an atypical antipsychotic drug, also known as second generation antipsychotic drug and is described in U.S. Pat. No. 4,804,663. It is practically insoluble in water, and sparingly soluble in 0.1 N HCl and methylene chloride.

Janssen-Ortho Inc markets extended release formulations of paliperidone, under the trade name of Invega® and are available in strengths of 1.5 mg, 3 mg, 6 mg and 9 mg. The said formulation employs an osmotic drug-release technology (OROS) to provide a "gradual ascending" drug delivery to minimize fluctuation in peak to trough concentration and permits 24 hour dosing interval.

WO2004010981 and EP1539115 disclose extended release formulations and methods for providing ascending rate of release of paliperidone utilizing a capsule-shaped tablet for once a day dosing. The dosage form utilizes a semipermiable membrane surrounding a three layer core: i) the first layer contains drug and an osmotic agent; ii) the middle layer contains higher amount of drug and without osmotic agent and iii) the third layer is a push layer containing osmotic agent. The capsule shaped tablet contains at least one orifice, which is drilled through the membrane on the first drug layer.

U.S. patent application 2006034927 discloses a paliperidone dosage form for sustained release of paliperidone comprising:
a delay layer comprising (i) a polymeric matrix, and (ii) microencapsulated drug, wherein the delay layer is substantially free of non-microencapsulated drug;
a second layer comprising (i) a polymeric matrix, and (ii) non-microencapsulated drug matrix; wherein the second layer is located adjacent to the delay layer.

U.S. patent application 20040092534 and U.S. patent application 20090202631 disclose a method for treating a condition responsive to paliperidone. The dosage form comprises:
(a) a capsule shaped tablet core comprising plurality of layers wherein at least one layer is a drug composition layer containing an active agent and at least one other layer comprises a suitable fluid-expandable polymer;
(b) a semipermeable membrane surrounding the capsule shaped tablet core to form a compartment having an osmotic gradient to drive fluid from an external fluid environment contacting the semipermeable membrane into the compartment; and
(c) an orifice formed through the semipermeable membrane and into the capsule shaped tablet core to permit the active agent to be released from within the compartment into the external fluid environment;
wherein the dosage form releases the active agent at a substantially ascending release rate for a prolonged period of time.

WO2009025859 relates to an extended release inlay tablet of paliperidone. The inlay tablet comprises at least an inlay core and outer layer wherein the inlay core comprises non-coated paliperidone and at least one polymer capable of swelling upon hydration and delaying the release of paliperidone from the inlay core. The inlay core optionally further comprises coated paliperidone. The outer layer partially surrounds the inlay core and comprises a pharmaceutical excipient which is substantially water insoluble.

WO2009109993 relates to extended release matrix compositions of micronized paliperidone, matrix agent and surfactant. The matrix agent is selected from insoluble release controlling agent or hydrophilic release controlling agent or fatty release controlling agent. In these compositions the surfactant and micronized paliperidone are essentially used to enhance the solubility of paliperidone. The particle size distribution of paliperidone is such that 90% particles of paliperidone are less than 30 micron, preferably less than 20 micron and more preferably less than 10 micron.

WO2010009900 relates to a solid pharmaceutical composition comprising monolithic matrix system (MMS) and/or multiparticulate matrix system (MPMS) comprising paliperidone and matrix forming agent. The matrix forming agent is more preferably present in an amount from 60-98% w/w of matrix particles that prolongs the release of paliperidone. The average particle diameter of paliperidone is in the range of 1-250 μm, preferably 5-150 μm. The composition further comprises surfactant and water penetration enhancer to improve the solubility of paliperidone.

WO2009026621 relates to particulates of paliperidone, or pharmaceutically acceptable salts thereof, having D50 particle size distribution of between about 1 micron to about 40 micron.

The compositions of the above mentioned prior art have one or more of the following essential requirements:
1. Use of surfactant and water penetration enhancer;
2. Use of excipient like osmogent;
3. Use of release controlling agent (matrix forming agent) which is preferably at least 60% by weight;
4. Additional process step of drilling an orifice through the semipermeable membrane to enable the release of drug from the system.

OBJECTS OF THE INVENTION

The main object of the present invention is to provide stabilized prolonged release solid oral compositions comprising paliperidone or a pharmaceutically acceptable salt thereof without incorporating surfactant and/or water penetration enhancer.

Another object of the invention is to provide such stabilized prolonged release compositions that exhibit desired in vitro dissolution profile of paliperidone or a pharmaceutically acceptable salt thereof with or without lag period.

It is yet another object of the invention to provide such compositions suitable for once a day administration.

It is yet another object of the invention to provide such compositions comprising paliperidone or a pharmaceutically acceptable salt thereof, wherein one or more release controlling agent (matrix forming agent) is present in less than 55% by weight of composition.

It is yet another object of the invention to provide a process for the preparation of such compositions comprising paliperidone or a pharmaceutically acceptable salt thereof.

DEFINITION

The term "lag period" as used herein means the time period wherein at the most 10% of atypical antipsychotic such as paliperidone or its pharmaceutically acceptable salt is released from the composition.

DETAILED DESCRIPTION OF THE INVENTION

The present invention is directed to stabilized prolonged release solid oral compositions comprising atypical antipsychotic such as paliperidone or pharmaceutically acceptable salts thereof without incorporating surfactant and/or water penetration enhancer in the composition and process for the preparation.

Such stabilized prolonged release compositions are preferably in the form of a matrix wherein one or more release controlling agents are present in and/or on the matrix.

The compositions further comprise at least one excipient selected from diluent, binder, lubricant, antioxidant, or mixtures thereof.

Such stabilized prolonged release compositions are suitable for once a day dosing to a patient in need thereof.

The release controlling agent present in and/or on the matrix is selected from at least one water soluble release controlling agent, water swellable release controlling agent, pH dependent release controlling agent, pH independent release controlling agent, or mixtures thereof.

In an embodiment of the invention, the release controlling agent is a water soluble release controlling agent.

In another embodiment of the invention, the release controlling agent is a water swellable release controlling agent.

In yet another embodiment of the invention, the release controlling agent is a pH dependent release controlling agent.

In yet another embodiment of the invention, the release controlling agent is a pH independent release controlling agent.

The composition of the present invention is designed in a manner to exhibit desired characteristics of dissolution profile, lag time, and solubility.

Compositions of the present invention do not require the use of surfactant and/or water penetration enhancer and yet achieve the desired dissolution profile in vitro. This is in sharp contrast to the prior art compositions that necessarily require surfactant and/or water penetration enhancer to achieve the desired dissolution profile.

The particle size distribution of paliperidone or its pharmaceutical acceptable salts thereof is such that 90% of particles are in the range from 1 micron to 250 microns, preferably in the range from 10 microns to 150 microns, more preferably in the range from 20 microns to 100 microns.

Paliperidone in the composition is in the range from 0.1% to 20% by weight of the composition, preferably from 0.5% to 15%, more preferably, from 1% to 10%, most preferably, 2% to 5% by weight of the composition.

The release controlling agent is selected from ionic release controlling agent, non ionic release controlling or mixtures thereof.

The release controlling agent is selected from one or more carbomer (e.g. carbopol 971 P, carbopol 71 G, carbopol 934 P and carbopol 974 P), one or more polyethylene oxide of molecular weight in the range of 1,000,000 to 7,000,000 (e.g. Polyox WSR303), xanthan gum, locust bean gum, guar gum, one or more hydroxylpropylmethylcellulose (of different viscosity grades from 100 cps to 250000 cps for 1% w/v aqueous solution), one or more hydroxypropyl cellulose (of different viscosity grades from 1000 cps to 4000 cps for 1% w/v aqueous solution), one or more hydroxylethylcellulose (of different viscosity grades from 700 cps to 10000 cps for 1% w/v aqueous solution), one or more ethyl cellulose (of different viscosity grades from 3 cps-100 cps for 5% w/v solution in mixture of toluene and alcohol), one or more carboxymethylcellulose, one or more sodium carboxymethylcellulose, one or more calcium carboxymethylethylcellulose, one or more methacrylic acid copolymers (commercially available as Eudragit E, Eudragit NE, Eudragit L, Eudragit S, Eudragit RL, Eudragit RS and Eudragit FS), mixture of polyvinyl acetate and polyvinyl pyrrolidone (commercially available as Kollidon SR or Kollicoat SR), one or more sodium alginate, hypromellose phthalate, polyvinyl acetate phthalate, hypromellose acetate succinate, cellulose acetate, cellulose acetate propionate, shellac, polyvinyl alcohol, polyvinyl acetate, or mixtures thereof.

Preferably, the release controlling agent is selected from one or more carbomer, one or more polyethylene oxide, hypromellose phthalate, ethyl cellulose, hydroxylpropylmethylcellulose, cellulose acetate, or mixtures thereof.

The release controlling agent is present in an amount from about 1% to about 55% by weight of the matrix, preferably from about 4% to 40% by weight of the matrix.

In one of the embodiments of the invention the release controlling agent is a part of the matrix.

In another embodiment of the invention the release controlling agent is present on the matrix for example as a coating layer.

In yet another embodiment of the invention the release controlling agent is present in and on the matrix.

The release controlling agent in the composition is a mixture of two or more release controlling agents. Preferably, the release controlling agent is the mixture of ionic release controlling agent and non ionic release controlling agent. Examples of such mixture include but not limited to the mixture of carbomer and polyethylene oxide, mixture of hydroxypropylmethyl cellulose phthalate and hydroxpropylmethyl cellulose, mixture of hydroxypropylmethyl cellulose phthalate and ethyl cellulose, mixture of carbomer and hydroxypropylmethyl cellulose.

The ratio of ionic release controlling agent to non ionic release controlling agent is from 1:0.5 to 1:1.

The coating layer on the matrix optionally includes one or more excipients selected from plasticizer, pigments, glidants, or mixtures thereof.

Plasticizer in the coating layer is selected from sorbitol, dibutyl sebacate, polyethylene glycol, triacetin, triethyl citrate, diethyl phthalate, dibutyl phthalate, miglyol, acetyl tributyl citrate, propylene glycol, hydrogenated oils, meglumine, cetyl alcohol, and mixtures thereof. Plasticizer in the coating layer is present in an amount from 2.5% to 30% by weight of the coating layer, preferably from 5% to 20% by weight, more preferably from 7.5% to 15% by weight, and most preferably from 9% to 11% by weight of the coating layer.

Coating layer is deposited on the tablet composition using a solvent selected from water, methanol, ethanol, isopropanol, acetone, dichloromethane or mixtures thereof. Diluents are selected from lactose, sugar, starches, modified starches, mannitol, sorbitol, inorganic salts, cellulose derivatives (e.g. microcrystalline cellulose, cellulose), calcium sulfate, calcium silicate, xylitol, lactitol, dibasic calcium phosphate, or mixtures thereof. Diluent is present in an amount from 10% to 90% by weight of the composition, preferably, from 20% to 70%, more preferably from 30% to 60% by weight of the composition, most preferably from 40% to 50% by weight of the composition.

Lubricants are selected from magnesium stearate, zinc stearate, stearic acid, palmitic acid, calcium stearate, talc, carnauba wax, hydrogenated vegetable oils, mineral oil, polyethylene glycols, sodium stearyl fumarate, or mixtures thereof.

Antioxidants are selected from butylated hydroxyl toluene, butylated hydroxyanisole, tocopherols (e.g alpha tocopherol), propyl gallate, ascorbates, ascorbic acid, sodium ascorbate, potassium or sodium salts of sulphurous acid (e.g. sodium sulphite, sodium bisulphite, sodium metabisulphite), or mixtures thereof.

Pigment, if present is selected from titanium dioxide, iron oxide (e.g iron oxide yellow, iron oxide red, iron oxide brown, iron oxide black) or mixtures thereof.

Glidant is selected from talc, magnesium stearate, starch, colloidal silicon dioxide, or mixtures thereof.

The process for preparation of stabilized prolonged release solid oral pharmaceutical compositions of paliperidone or a pharmaceutically acceptable salt thereof, wherein the process involves steps of:
a) mixing paliperidone or pharmaceutically acceptable salt thereof, diluent and optionally at least one ingredient selected from antioxidant, lubricant, glidant, release controlling agent, or mixtures thereof;
b) optionally converting the mixture of step a) into granules;
c) optionally mixing the granules with release controlling agent;
d) compressing the mixture of step a) or b) or c) to obtain a matrix;
e) optionally coating the matrix of step d) with at least one release controlling agent.

The matrix in step d) is preferably a tablet.

In one of the embodiments of the present invention the process for preparation of stabilized prolonged release solid oral pharmaceutical compositions of paliperidone or a pharmaceutically acceptable salt thereof involves steps of:
a) mixing of paliperidone or pharmaceutically acceptable salt thereof one or more of diluents and optionally at least one excipient selected from binders, lubricants, antioxidants, or mixtures thereof;
b) granulating the mixture with suitable solvent followed by drying and grading to obtain granules;
c) mixing of the granules obtained in step b) with at least one release controlling agent;
d) lubricating the mixture obtained in step c) with lubricants;
e) compressing the lubricated mixture obtained in step d) into matrix tablets;
f) optionally coating the compressed tablets of step e) with at least one release controlling agent.

In another embodiment of the present invention the process for preparation of stabilized prolonged release solid oral pharmaceutical compositions of paliperidone or a pharmaceutically acceptable salt thereof involves steps of:
a) mixing paliperidone or pharmaceutically acceptable salt thereof, at least one release controlling agent, and at least one excipient selected from one or more of diluents, binders, antioxidants, or mixtures thereof;
b) granulating the mixture of step a) with a suitable solvent followed by drying and grading to obtain granules;
c) lubricating the granules obtained in step b) with lubricants;
d) compressing the lubricated mixture obtained in step c) into tablets;
e) optionally coating the compressed tablets of step d) with at least one release controlling agent.

In yet another embodiment of the present invention the process for preparation of stabilized prolonged release solid oral pharmaceutical compositions of paliperidone or a pharmaceutically acceptable salt thereof involves steps of:
a) mixing paliperidone or pharmaceutically acceptable salt thereof, at least one release controlling agent, and at least one excipient selected from one or more of diluents, binders, antioxidants, or mixtures thereof;
b) lubricating the mixture obtained in step a) with lubricants;
c) compressing the lubricated mixture obtained in step b) into tablets;
d) optionally coating the compressed tablets of step d) with at least one release controlling agent.

In yet another embodiment of the present invention the process for preparation stabilized prolonged release solid oral pharmaceutical compositions of paliperidone or a pharmaceutically acceptable salt thereof involves steps of:
a) mixing of paliperidone or pharmaceutically acceptable salt thereof, at least one release controlling agent and at least one excipient selected from one or more of diluents, binders, antioxidants, or mixtures thereof to obtain mixture;
b) compressing or compacting the mixture to form a matrix followed by milling to obtain granules;
c) lubricating the granules obtained in step b) with lubricants;
d) compressing the lubricated mixture obtained in step c) into tablet;
e) optionally coating the compressed tablets of step d) with at least one release controlling agent.

The prolonged release solid oral pharmaceutical compositions prolongs the release of paliperidone or a pharmaceutically acceptable salt thereof over a period of at least 12 hours, preferably upto 24 hours.

The composition comprising release controlling agent exhibits desired in vitro release of paliperidone or a pharmaceutically acceptable salt thereof with or without lag period.

Compositions based on one of the embodiments of the invention exhibits desired in vitro release of paliperidone or a pharmaceutically acceptable salt thereof without any lag period.

In another embodiment, the composition exhibits desired in vitro release of paliperidone or a pharmaceutically acceptable salt thereof after the lag period of at least 2 hours.

In yet another embodiment, the composition exhibits desired in vitro release of paliperidone or a pharmaceutically acceptable salt thereof after the lag period of at least 3 hours.

In yet another embodiment, the composition exhibits desired in vitro release of paliperidone or a pharmaceutically acceptable salt thereof after the lag period of at least 4 hours.

In yet another embodiment, the composition exhibits desired in vitro release of paliperidone or a pharmaceutically acceptable salt thereof after the lag period of at least 5 hours.

In yet another embodiment, the composition exhibits desired in vitro release of paliperidone or a pharmaceutically acceptable salt thereof after the lag period of at least 6 hours.

The prolonged release tablets comprising paliperidone or a pharmaceutically acceptable salt thereof were subjected to accelerated stability testing and were found to be stable at least for the period of 3 months at 40° C. and 75% RH.

The invention is illustrated with non limiting examples.

EXAMPLES (I-III)

Paliperidone, butylated hydroxytoluene, microcrystalline cellulose, polyethylene oxide and carbopol and colloidal silicon dioxide were sifted and mixed in an octagonal blender for 20 minutes at 24 RPM. Magnesium stearate was added to and the resulting mixture was compressed into tablets.

Coated Tablets of Ex. I-II

Ethyl cellulose and hypromellose phthalate were dispersed and dissolved in the mixture of isopropyl alcohol and methylene chloride. Dibutyl sebacate and talc were added to the solution to obtain dispersion. The resulting dispersion was filtered and sprayed on the tablets.

Coated Tablets of Ex. III

Cellulose acetate and polyethylene glycol was dissolved in the mixture of methylene chloride and methanol. Sorbitol was dissolved in purified water and was added to the above solution. Talc was added to the resulting solution to obtain dispersion. The resulting dispersion was filtered and sprayed on the tablets.

The examples following above mentioned process is given in table I.

TABLE I

| No. | Ingredients | Ex. I % w/w | Ex. II % w/w | Ex. III % w/w |
|---|---|---|---|---|
| 1. | Paliperidone | 2.86 | 2.82 | 2.86 |
| 2. | Polyethylene oxide (PEO WSR 303 LEO) | 19.05 | 18.78 | 19.05 |
| 3. | Carbopol 71 G | 19.05 | 18.78 | 19.05 |
| 4. | Microcrystalline cellulose | 49.48 | 48.78 | 49.48 |
| 5. | Butylated hydroxytoluene | 0.05 | 0.05 | 0.05 |
| 6. | Colloidal silicon dioxide | 2.38 | 2.35 | 2.38 |
| 7. | Magnesium stearate | 2.38 | 2.35 | 2.38 |
| 8. | Hypromellose phthalate | 2.60 | 3.33 | — |
| 9. | Ethyl cellulose | 1.30 | 1.67 | — |
| 10. | Cellulose acetate | — | — | 3.78 |
| 11. | Dibutyl sebacate | 0.49 | 0.62 | — |
| 12. | Polyethylene glycol | — | — | 0.38 |
| 13. | Sorbitol | — | — | 0.38 |
| 14. | Talc | 0.38 | 0.49 | 0.23 |

EXAMPLE IV

Paliperidone, mannitol and lactose were sifted and mixed for 10 minutes. The resulting mixture was granulated with povidone solution in isopropyl alcohol to obtain granules. The granules were dried at 50° C. in fluid bed processor. The dried granules were sifted and lubricated with colloidal silicon dioxide, magnesium stearate and talc for 10 min. The lubricated mixture was compressed into the tablets. Cellulose acetate and polyethylene glycol was dissolved in the mixture of methylene chloride and methanol. Sorbitol was dissolved in purified water and was added to the above solution. Talc was added to the resulting solution to obtain dispersion. The resulting dispersion was sprayed on the tablets.

The example following above mentioned process is given in table II.

TABLE II

| No. | Ingredients | Ex. IV % w/w |
|---|---|---|
| 1. | Paliperidone | 3.95 |
| 2. | Mannitol | 39.47 |
| 3. | Lactose anhydrous | 44.47 |
| 4. | Povidone | 4.47 |
| 5. | Talc | 0.99 |
| 6. | Colloidal silicon dioxide | 0.39 |
| 7. | Magnesium stearate | 0.99 |
| 8. | Cellulose acetate 398-10 | 4.17 |
| 9. | Polyethylene glycol 400 | 0.41 |
| 10. | Sorbitol | 0.41 |
| 11. | Talc | 0.26 |

EXAMPLE V-VI

Paliperidone, butylated hydroxytoluene, microcrystalline cellulose, polyethylene oxide and carbopol and colloidal silicon dioxide were sifted and mixed in an octagonal blender for 20 minutes at 24 RPM. Magnesium stearate was added and the resulting mixture was compressed into tablets. Ethyl cellulose and hypromellose phthalate were dispersed and dissolved in the mixture of isopropyl alcohol and methylene chloride. Dibutyl sebacate and talc were added to the above solution to obtain dispersion. The resulting dispersion was filtered and sprayed on the tablets.

Examples following above mentioned process are given in table III.

TABLE III

| No. | Ingredients | Ex. V % w/w | Ex. VI % w/w |
|---|---|---|---|
| 1. | Paliperidone | 8.45 | 12.68 |
| 2. | Polyethylene oxide | 18.78 | 18.78 |
| 3. | Carbopol 71 G | 18.78 | 18.78 |
| 4. | Microcrystalline cellulose | 43.10 | 38.87 |
| 5. | Butylated hydroxytoluene | 0.09 | 0.09 |
| 6. | Colloidal silicon dioxide | 2.35 | 2.35 |
| 7. | Magnesium stearate | 2.35 | 2.35 |
| 8. | Hypromellose phthalate | 3.05 | 3.05 |
| 9. | Ethyl cellulose 45 cps | 1.53 | 1.53 |
| 10. | Dibutyl sebacate | 0.57 | 0.57 |
| 11. | Talc | 0.45 | 0.45 |
| 12. | Titanium dioxide | 0.51 | 0.51 |

EXAMPLE (VII-VIII)

Paliperidone, butylated hydroxytoluene, microcrystalline cellulose, colloidal silicon dioxide, polyethylene oxide and carbopol (Ex. VIII) or hypromellose K4M (Ex. IX) were sifted and mixed in an octagonal blender for 20 minutes at 24 RPM. Magnesium stearate was added and the resulting mixture was compressed into tablets.

The examples following above mentioned process are given in table IV.

TABLE IV

| No. | Ingredients | Ex VII % w/w | Ex VIII % w/w |
|---|---|---|---|
| 1. | Paliperidone | 3 | 3 |
| 2. | Polyethylene oxide (PEO WSR 303LEO) | 20 | 20 |
| 3. | Carbopol 71 G | 20 | — |
| 4. | Hypromellose K4M | — | 20 |
| 5. | Microcrystalline cellulose | 51.95 | 51.95 |
| 6. | Butylated hydroxytoluene | 0.05 | 0.05 |
| 7. | Colloidal silicon dioxide | 2.5 | 2.5 |
| 8. | Magnesium stearate | 2.5 | 2.5 |

Dissolution Profile

The tablets prepared as per examples I-VIII were analyzed in vitro using USP II paddle apparatus, at 50 rpm, Volume: 500 ml, using 0.2% w/w NaCl and 0.0825 N HCL (pH 1.2) at 37° C. The cumulative drug release profiles of these tablets are depicted in FIG. 1:

Stability Data

The tablets prepared as per example I were packed in HDPE container containing molecular sieve and were subjected to accelerated stability conditions at 40° C./75% RH. The dissolution profile and the impurity profile at the end of three months of accelerated stability testing were as follows:

Dissolution Profile

| Time | Cumulative % drug release profile | |
|---|---|---|
| (Hrs.) | Initial | 3 Month, 40° C./75% RH |
| 1 | 0 | 0 |
| 6 | 10 | 4 |
| 14 | 51 | 44 |
| 24 | 84 | 77 |

Impurity Profile

| Impurity | Initial | 3 Month |
|---|---|---|
| Impurity A | ND | ND |
| Impurity B | ND | ND |
| Impurity H | 0.08% | 0.11% |
| Single maximum unknown impurity | 0.01% | 0.45% |
| Total unknown impurity | 0.03% | 1.2% |
| Total impurity | 1.03% | 1.31% |

The above data reveals that there was no appreciable change in the drug release profile and impurity profile at the end of three months at accelerated stability conditions of 40° C./75% RH and the tablets were stable at least for the period of three months.

We claim:

1. A stabilized prolonged release surfactant-free solid oral paliperidone tablet composition that upon dissolution testing releases 10% or less of paliperidone in at least two hours, the tablet composition comprising:
   (i) a matrix core tablet, wherein the matrix core tablet comprises:
   (a) paliperidone in the amount of about 2.82% to about 12.68% of the tablet composition weight;
   (b) release controlling agents polyethylene oxide and a granulated-free flowing cross-linked polyacrylate polymer in the ratio of about 1:1 by weight, the agents comprising together about 37.56% to about 38.10% of the tablet composition weight;
   (c) diluent microcrystalline cellulose comprising about 38.87% to about 49.48% of the tablet composition weight;
   (d) antioxidant butylated hydroxyl toluene in the amount of about 0.05% to about 0.09% of the tablet composition weight;
   (e) lubricant magnesium stearate in the amount of about 2.35% to about 2.38% of the tablet composition weight;
   (f) glidant colloidal silicon dioxide in the amount of about 2.35% to about 2.38% of the tablet composition weight;
   (ii) a coating layer coated on the said matrix core tablet, wherein the coating layer comprises:
   (a) release controlling agents comprising a mixture of hypromellose phthalate and ethyl cellulose in a ratio of about 1:0.5, the mixture comprising in total about 3.90% to about 5% of the tablet composition weight;
   (b) plasticizer dibutyl sebacate comprising from about 0.49% to about 0.62% of the tablet composition weight; and
   (c) talc comprising from about 0.38 to 0.49% of the tablet composition weight.

2. A process for making a stabilized prolonged release surfactant-free solid oral pharmaceutical composition of claim 1 comprising the steps of:
   a) mixing a paliperidone or pharmaceutically acceptable salt thereof in the amount of 2.82% to about 12.68% of the tablet composition weight, diluent microcrystalline cellulose in amount of 38.87% to 49.48% by weight of the tablet composition, antioxidant butylated hydroxyl toluene in the amount of 0.05% to about 0.09% of the tablet composition by weight, lubricant magnesium stearate in the amount of 2.35% to about 2.38% of the tablet composition by weight, glidant colloidal silicon dioxide in the amount of about 2.35% to about 2.38% of the tablet composition weight, and release controlling agents polyethylene oxide and a granulated-free flowing cross-linked polyacrylate polymer in the ratio of about 1:1 by weight, the agents comprising together about 37.56% to about 38.10% of the tablet composition weight;
   b) compressing the mixture to obtain a matrix; and
   c) coating the matrix with a mixture comprising release controlling agent, plasticizer dibutyl sebacate, and talc wherein the release controlling agent comprises a mixture of hypromellose phthalate and ethyl cellulose in a ratio of about 1:0.5 comprising 3.90% to about 5% of the tablet composition by weight, the plasticizer dibutyl sebacate comprises from about 0.49% to about 0.62% of the tablet composition weight, and the talc comprises from about 0.38 to 0.49% of the tablet composition weight.

3. The paliperidone tablet composition of claim 1 that upon dissolution testing releases 10% or less of paliperidone in at least three hours.

4. The paliperidone tablet composition of claim 1 that upon dissolution testing releases 10% or less of paliperidone in at least four hours.

5. The paliperidone tablet composition of claim 1 that upon dissolution testing releases 10% or less of paliperidone in at least five hours.

6. The paliperidone tablet composition of claim 1 that upon dissolution testing releases 10% or less of paliperidone in at least six hours.

7. The prolonged release surfactant-free solid oral paliperidone tablet composition of claim 1, the tablet composition comprising:
   (i) a matrix core tablet, wherein the matrix core tablet comprises:
   (a) paliperidone in the amount of about 2.86% of the tablet composition weight;

(b) release controlling agents polyethylene oxide and a granulated-free flowing cross-linked polyacrylate polymer in the ratio of about 1:1 by weight, the agents comprising together about 38.10% of the tablet composition weight;
(c) diluent microcrystalline cellulose comprising about 49.48% of the tablet composition weight;
(d) antioxidant butylated hydroxyl toluene in the amount of about 0.05% of the tablet composition weight;
(e) lubricant magnesium stearate in the amount of about 2.38% of the tablet composition weight;
(f) glidant colloidal silicon dioxide in the amount of about 2.38% of the tablet composition weight;
(ii) a coating layer coated on the said matrix core tablet, wherein the coating layer comprises:
(a) release controlling agents comprising a mixture of hypromellose phthalate and ethyl cellulose in a ratio of about 1:0.5, the mixture comprising in total about 3.90% of the tablet composition weight;
(b) plasticizers dibutyl sebacate comprising from about 0.49% of the tablet composition weight; and
(c) talc comprising from about 0.38% of the tablet composition by weight.

8. The prolonged release surfactant-free solid oral paliperidone tablet composition of claim 1, the tablet composition comprising:
(i) a matrix core tablet, wherein the matrix core tablet comprises:
(a) paliperidone in the amount of about 2.82% of the tablet composition weight;
(b) release controlling agents polyethylene oxide and a granulated-free flowing cross-linked polyacrylate polymer in the ratio of about 1:1 by weight, the agents comprising together about 37.56% of the tablet composition weight;
(c) diluent microcrystalline cellulose comprising about 48.78% of the tablet composition weight;
(d) antioxidant butylated hydroxyl toluene in the amount of about 0.05% of the tablet composition weight;
(e) lubricant magnesium stearate in the amount of about 2.35% of the tablet composition weight;
(f) glidant colloidal silicon dioxide in the amount of about 2.35% of the tablet composition weight;
(ii) a coating layer coated on the said matrix core tablet, wherein the coating layer comprises:
(a) release controlling agents comprising a mixture of hypromellose phthalate and ethyl cellulose in a ratio of about 1:0.5, the mixture comprising in total about 5% of the tablet composition weight;
(b) plasticizer dibutyl sebacate comprising from about 0.62% of the tablet composition weight; and
(c) talc comprising about 0.49% of the tablet composition by weight.

9. The prolonged release surfactant-free solid oral paliperidone tablet composition of claim 1, the tablet composition comprising:
(i) a matrix core tablet, wherein the matrix core tablet comprises:
(a) paliperidone in the amount of about 8.45% or about 12.68% of the tablet composition weight;
(b) release controlling agents polyethylene oxide and a granulated-free flowing cross-linked polyacrylate polymer in the ratio of about 1:1 by weight, the agents comprising together about 37.56% of the tablet composition weight;
(c) diluent microcrystalline cellulose comprising about 43.10% or about 38.87% of the tablet composition weight;
(d) antioxidant butylated hydroxyl toluene in the amount of about 0.09% of the tablet composition weight;
(e) lubricant magnesium stearate in the amount of about 2.35% of the tablet composition weight;
(f) glidant colloidal silicon dioxide in the amount of about 2.35% of the tablet composition weight;
(ii) a coating layer coated on the said matrix core tablet, wherein the coating layer comprises:
(a) release controlling agents comprising a mixture of hypromellose phthalate and ethyl cellulose in a ratio of about 1:0.5, the mixture comprising in total about 4.58% of the tablet composition weight; and
(b) plasticizer dibutyl sebacate comprising from about 0.57% of the tablet composition weight; and
(c) talc comprising from about 0.45% of the tablet composition.

* * * * *